(12) United States Patent
Smith

(10) Patent No.: US 6,364,904 B1
(45) Date of Patent: Apr. 2, 2002

(54) HELICALLY FORMED STENT/GRAFT ASSEMBLY

(75) Inventor: Scott Smith, Chaska, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/345,026

(22) Filed: Jul. 2, 1999

(51) Int. Cl.[7] .................................................. A61F 2/06
(52) U.S. Cl. ..................................... 623/1.22; 623/1.13
(58) Field of Search ........................... 623/1, 2, 11, 12, 623/1.1, 1.13, 1.15, 1.22

(56) References Cited

U.S. PATENT DOCUMENTS

| 4,313,231 | A |   | 2/1982  | Koyamada          |        |
|-----------|---|---|---------|-------------------|--------|
| 5,108,417 | A | * | 4/1992  | Sawyer            | 623/1  |
| 5,123,917 | A |   | 6/1992  | Lee               |        |
| 5,443,496 | A | * | 8/1995  | Schwartz et al.   |        |
| 5,500,013 | A | * | 3/1996  | Buscemi et al.    | 623/1  |
| 5,607,478 | A | * | 3/1997  | Lentz et al.      | 623/12 |
| 5,766,237 | A | * | 6/1998  | Cragg             |        |
| 5,782,904 | A |   | 7/1998  | White et al.      |        |
| 5,810,870 | A |   | 9/1998  | Myers et al.      |        |
| 5,824,040 | A |   | 10/1998 | Smith             |        |
| 5,843,173 | A |   | 12/1998 | Shannon et al.    |        |
| 5,897,587 | A |   | 4/1999  | Martakos et al.   |        |
| 5,925,075 | A |   | 7/1999  | Myers et al.      |        |
| 5,928,279 | A | * | 7/1999  | Shannon et al.    |        |
| 6,063,111 | A | * | 5/2000  | Hieshima et al.   | 623/1  |

FOREIGN PATENT DOCUMENTS

| DE | 19531659 A1 | 3/1997 |
| WO | WO 98/27894 | 2/1998 |
| WO | WO 98/27893 | 7/1998 |
| WO | WO 99/32051 | 7/1999 |

* cited by examiner

Primary Examiner—David J. Isabella
(74) Attorney, Agent, or Firm—Hoffmann & Baron, LLP

(57) ABSTRACT

The present invention relates to a support structure/membrane composite device which includes a support structure, such as a radially expandable stent, a porous non-textile polymeric membrane adjacent to said stent and a thermoplastic anchor means attaching said stent to said porous non-textile polymeric membrane. The porous non-textile polymeric membrane is preferably made from expandable fluoropolymer materials. The anchoring means is a thermoplastic material which is dissolvable at the interface between the support structure and membrane by a suitable solvent which wets the membrane surface and deposits the thermoplastic material within the pores of the membrane. Methods of preparing the device are also disclosed.

15 Claims, 20 Drawing Sheets

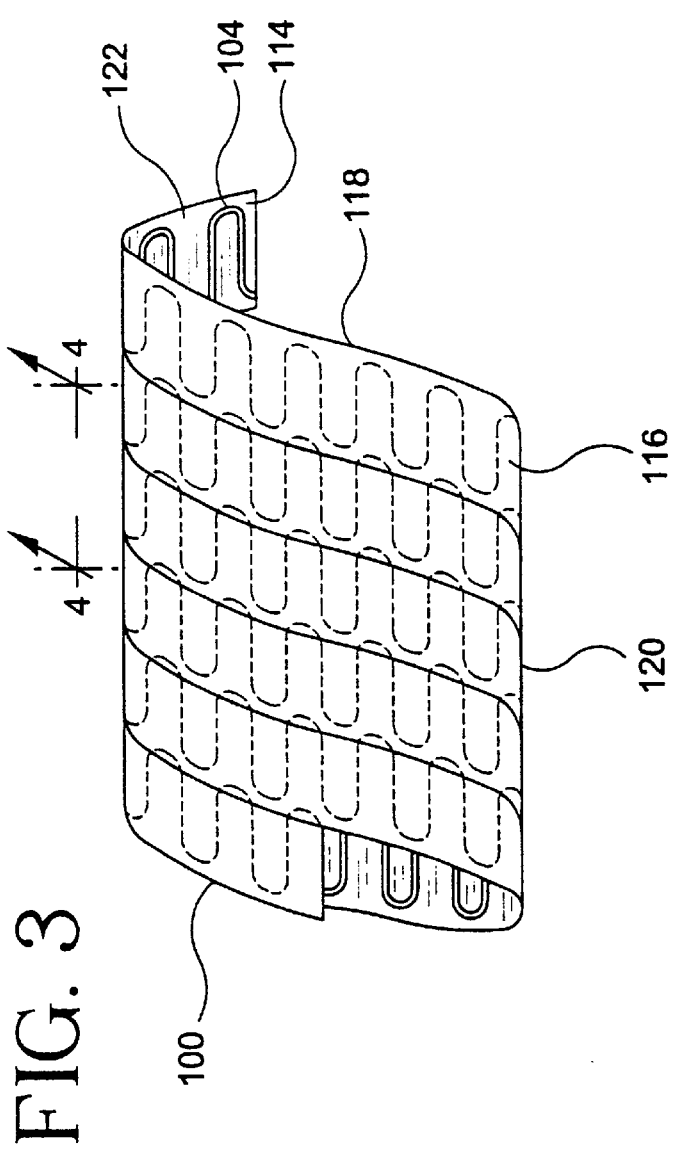
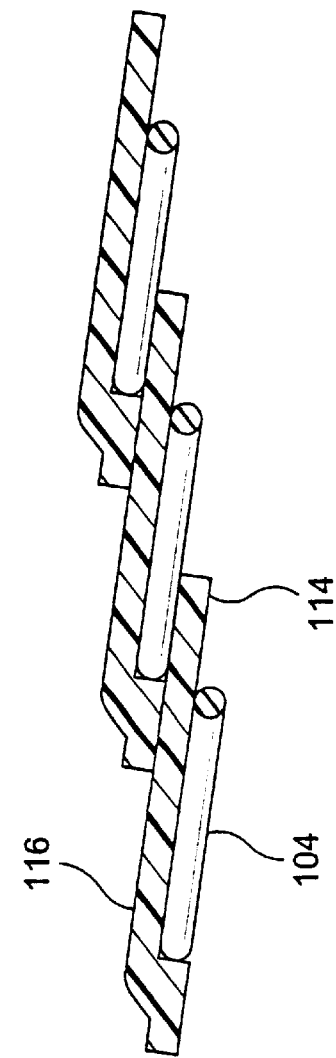

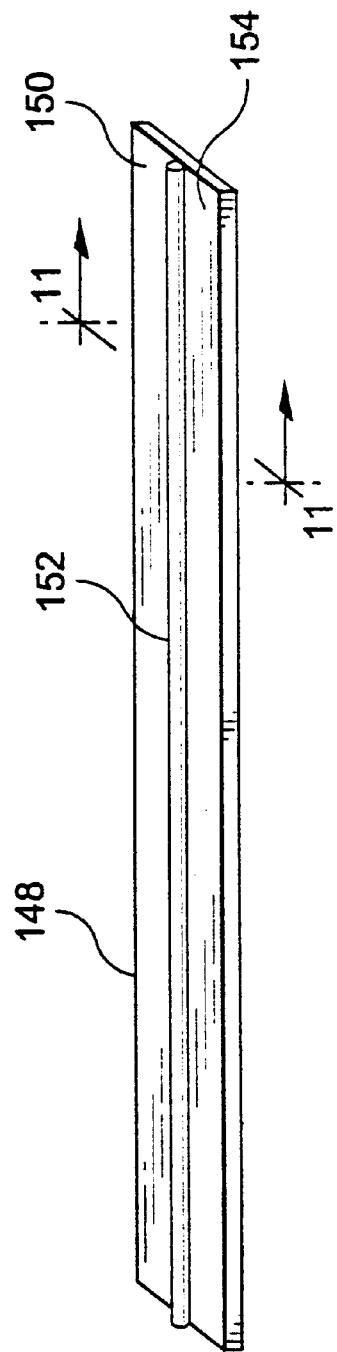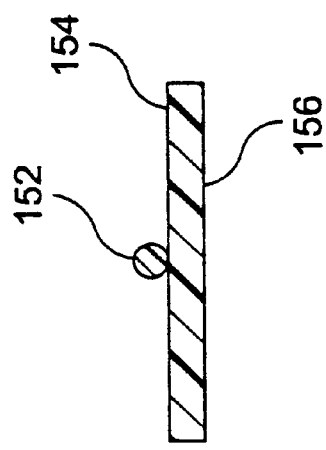

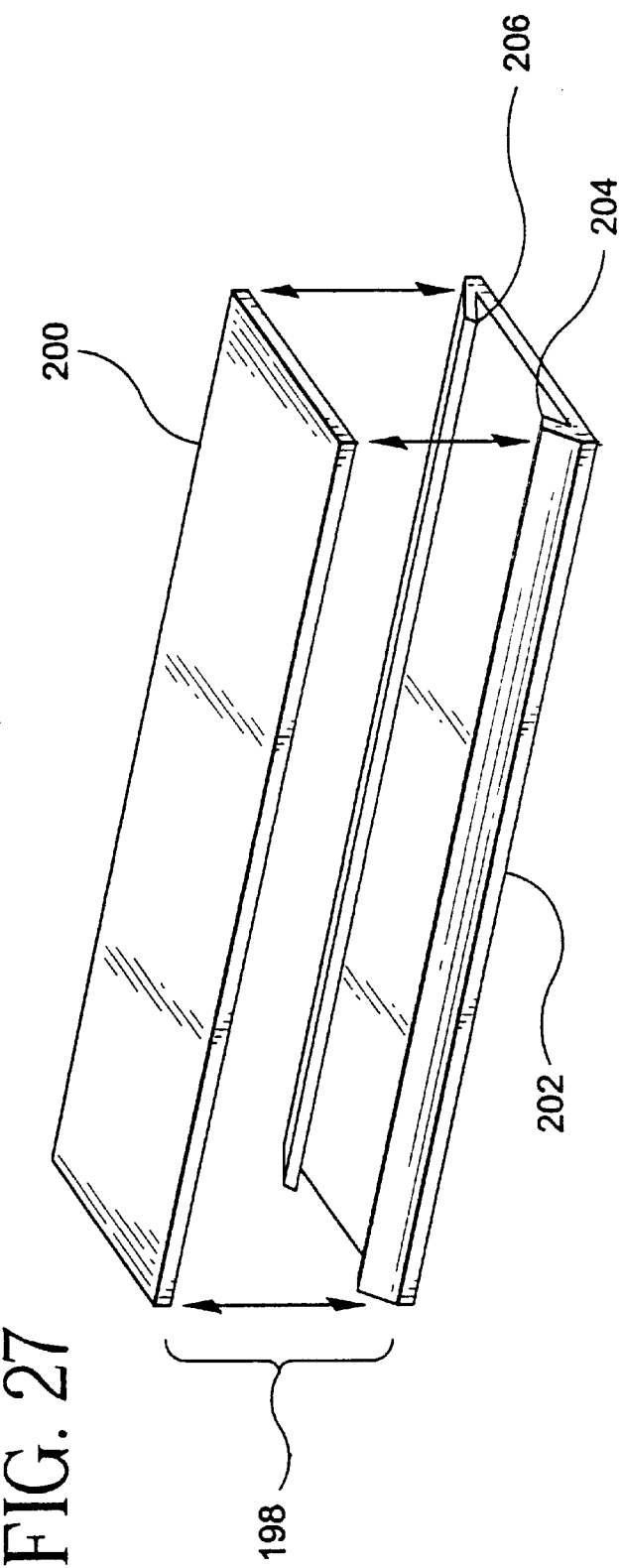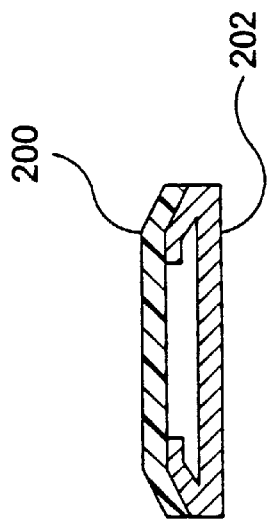
FIG. 27
FIG. 28

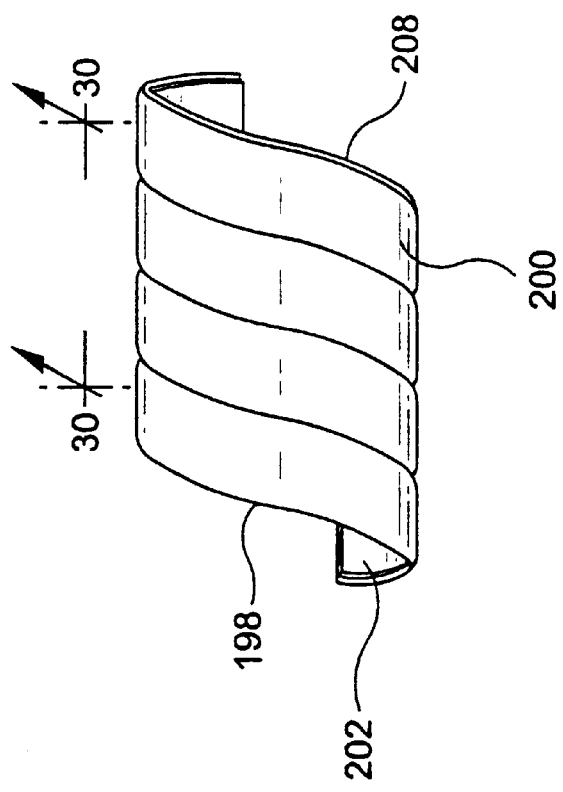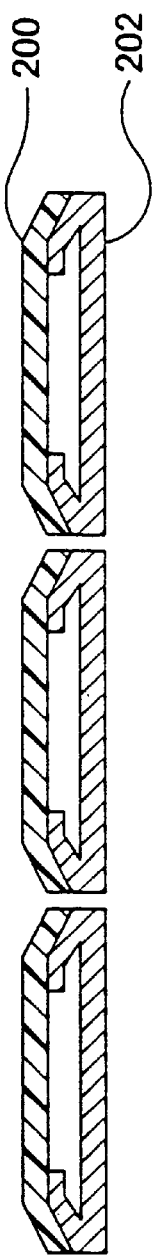

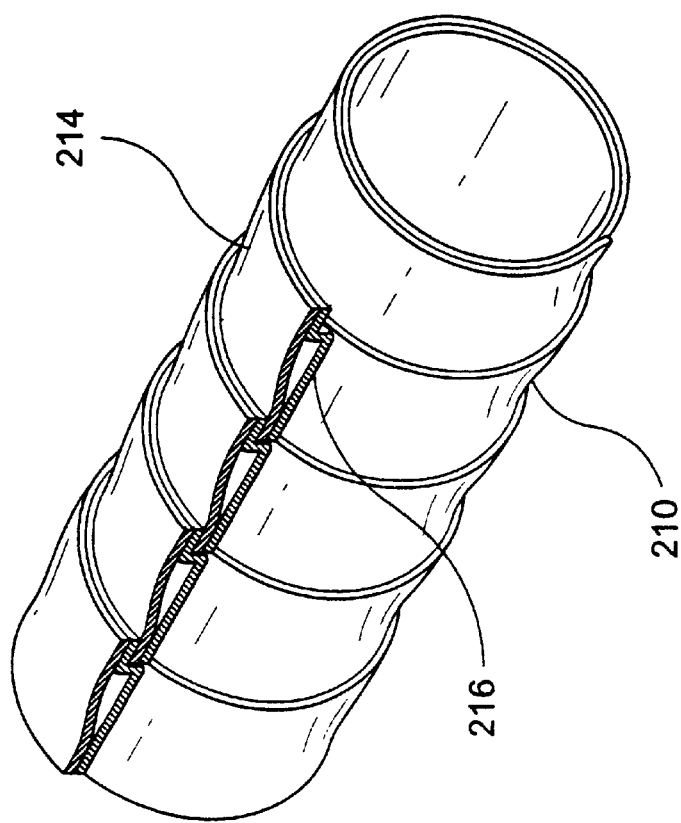

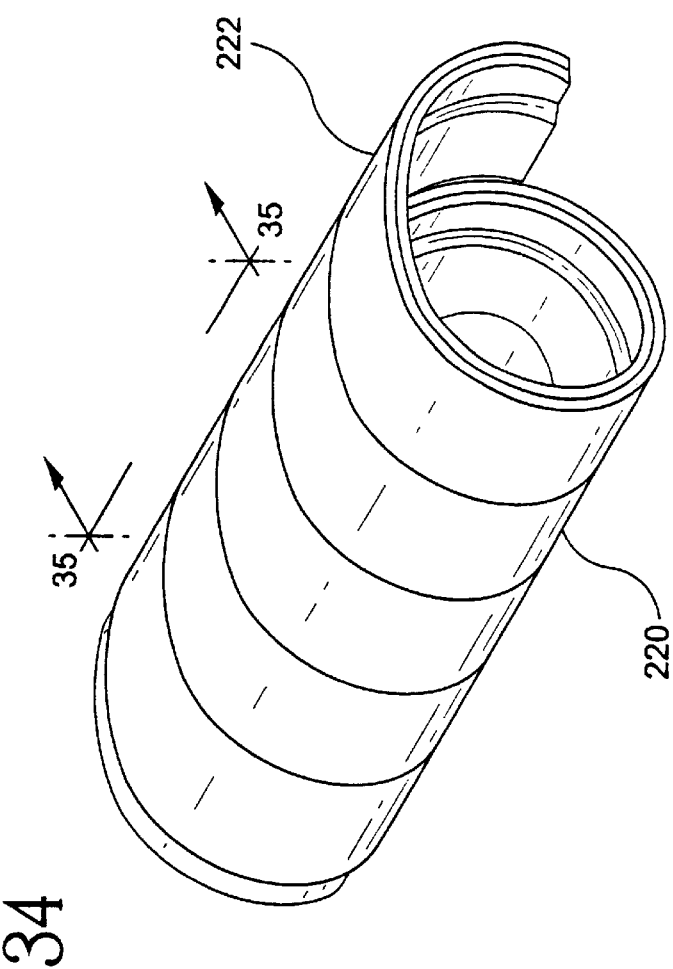
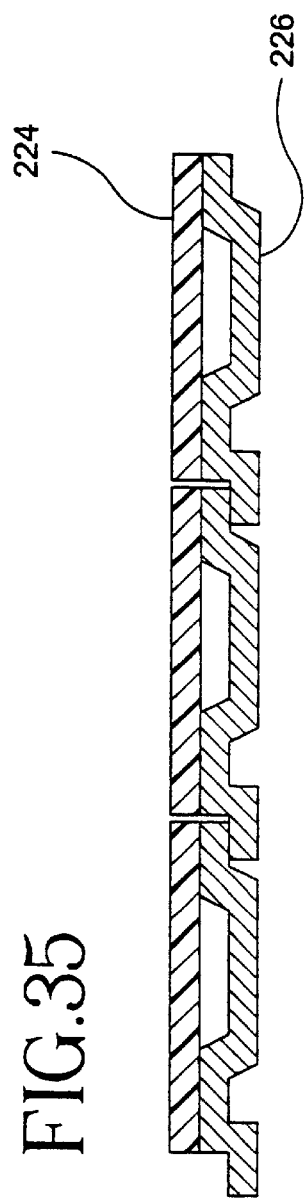
FIG. 34
FIG. 35

HELICALLY FORMED STENT/GRAFT ASSEMBLY

FIELD OF THE INVENTION

The present invention relates to a tubular stent/graft apparatus. More particularly, the present invention relates to a composite intraluminal device including a helically formed tubular stent/graft assembly formed from a planar pre-assembly having a wire stent material laminated between ePTFE strips.

BACKGROUND OF THE INVENTION

An intraluminal prosthesis is a medical device commonly known to be used in the treatment of diseased blood vessels. An intraluminal prosthesis is typically used to repair, replace, or otherwise correct a damaged blood vessel. An artery or vein may be diseased in a variety of different ways. The prosthesis may therefore be used to prevent or treat a wide variety of defects such as stenosis of the vessel, thrombosis, occlusion, or an aneurysm.

One type of endoluminal prosthesis used in the repair of diseases in various body vessels is a stent. A stent is a generally longitudinal tubular device formed of biocompatible material which is useful to open and support various lumens in the body. For example, stents may used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open ended and are radially expandable between a generally unexpended insertion diameter and an expanded implantation diameter which is greater than the unexpended insertion diameter. Stents are often flexible in configuration, which allows them to be inserted through and conform to tortuous pathways in the blood vessel. The stent is generally inserted in a radially compressed state and expanded either through a self-expanding mechanism, or through the use of balloon catheters.

A graft is another type of commonly known type of intraluminal prosthesis which is used to repair and replace various body vessels. A graft provides an artificial lumen through which blood may flow. Grafts are tubular devices which may be formed of a variety of material, including textiles, and non-textile materials. One type of non-textile material particularly useful as an implantable intraluminal prosthesis is polytetrafluoroethylene (PTFE). PTFE exhibits superior biocompatability and low thrombogenicity, which makes it particularly useful as vascular graft material in the repair or replacement of blood vessels. In vascular applications, the grafts are manufactured from expanded polytetrafluoroethylene (ePTFE) tubes. Such tubular grafts may be formed from extruded tubes, sheets or films. These tubes have a microporous structure which allows natural tissue ingrowth and cell endothelization once implanted in the vascular system. This contributes to long term healing and patency of the graft.

Grafts formed of ePTFE have a fibrous state which is defined by interspaced nodes interconnected by elongated fibrils. The spaces between the node surfaces that is spanned by the fibrils is defined as the internodal distance (IND). Porosity of a graft is measured generally by IND. In order of proper tissue ingrowth and cell endothelization, grafts must have sufficient porosity obtained through expansion. When the term expanded is used to describe PTFE, it is intended to describe PTFE which has been stretched, in accordance with techniques which increase IND and concomitantly porosity. The stretching may be in uni-axially, bi-axially, or multi-axially. The nodes are spaced apart by the stretched fibrils in the direction of the expansion. Properties such as tensile strength, tear strength and radial (hoop) strength are all dependent on the expansion process. Expanding the film by stretching it in two directions that are substantially perpendicular to each other, for example longitudinally and transversely, creates a biaxially oriented material. Films having multi-axially-oriented fibrils may also be made by expanding the film in more than two directions. Porous ePTFE grafts have their greatest strength in directions parallel to the orientation of their fibrils. With the increased strength, however, often comes reduced flexibility.

While ePTFE has been described above as having desirable biocompatability qualities, tubes comprised of ePTFE, as well as films made into tubes, tend to exhibit axial stiffness, and minimal radial compliance. Longitudinal compliance is of particular importance to intraluminal prosthesis as the device must be delivered through tortuous pathways of a blood vessel to the implantation site where it is expanded. A reduction in axial and radial flexibility makes intraluminal delivery more difficult.

Composite intraluminal prosthesis are known in the art. In particular, it is known to combine a stent and a graft to form a composite medical device. Such composite medical devices provide additional support for blood flow through weakened sections of a blood vessel. In endovascular applications the use of a composite graft or a stent/graft combination is becoming increasingly important because the combination not only effectively allows the passage of blood therethrough, but also ensures patency of the implant.

However, in each of the above described sheet or film cases, the stent and the graft are separately formed and then attached. This manner of construction results in potential separation of the graft from the stent because it is difficult to affix tubular structures to one and another.

The present invention seeks to provide a more efficient and predictable means of forming a stent/graft assembly by forming the tubular covering and tubular stent simultaneously.

SUMMARY OF THE INVENTION

It is an object of the present invention to provide an improved composite stent/graft apparatus.

It is a further object of the present invention to provide tubular stent/graft devices that can be manufactured by continuous techniques.

It is a further object of the present invention to produce the assembly strips in a continuous manufacturing technique to reduce the cost of manufacturing the tubular stent/grafts.

It is still a further object of the present invention to provide a tubular stent/graft that has consistent wall properties without undesired seams, bumps or weak points.

In the efficient attainment of these and other objects, the present invention provides a tubular stent/graft apparatus comprising a planar graft material having a planar stent wire attached to one of its sides to form a strip assembly. The strip assembly is helically wound to form a tubular stent/graft structure.

The stent may be radially expandable, and the stent may be chosen from a wide variety of stent materials and configurations. For example, the stent may be self-expandable, balloon expandable or made from a memory alloy, the configuration of which can be controlled by temperature.

The present invention further relates to a method of making a tubular stent/graft assembly comprising the steps of (i) forming a substantially planar strip and wire assembly comprising planar graft material formable into a graft and planar stent wire formable into a radially adjustable stent, wherein the wire is attached lengthwise along the length of said planar strip; and (ii) helically winding the substantially planar strip and wire assembly to form said tubular stent graft assembly.

BRIEF DESCRIPTION OF THE DRAWINGS

FIG. 3 is a perspective of a portion of a continuous tubular stent/graft structure formed by helically winding the assembly strip of FIG. 1.

FIG. 4 is a cross-sectional view of a portion of the tubular stent/graft structure of FIG. 3 taken along line 4—4.

FIG. 10 is a perspective showing of a further embodiment of an assembly strip of the present invention containing a graft strip and a straight wire for forming a tubular stent/graft structure for use as an intraluminal device.

FIG. 11 is a cross-sectional view of the assembly strip of FIG. 10 taken along line 11—11.

FIG. 27 is an exploded perspective view of an assembly strip of the present invention having a planar graft strip and a cuffed planar ribbon stent strip for forming a continuous tubular stent/graft structure.

FIG. 28 is a cross-sectional view of the assembly strip of FIG. 27.

FIG. 29 is an illustration of a portion of a continuous tubular stent/graft structure formed by helically winding the assembly strip of FIG. 27.

FIG. 30 is a cross-sectional view of a portion of the continuous tubular stent/graft structure of FIG. 29 taken along line 30—30.

FIG. 31 is a perspective showing, partially in section, of an assembly strip having a planar graft strip and a planar ribbon stent strip with a longitudinal fold for forming a tubular stent/graft structure.

FIG. 32 is a perspective showing, partially in section, of a tubular stent/graft structure having a substantially continuous luminal surface formed by helically winding the assembly strip of FIG. 31.

FIG. 34 is an illustration of a portion of a tubular stent/graft structure having a substantially continuous exterior surface formed by helically winding the assembly strip of FIG. 33.

FIG. 35 is a cross-sectional view of a portion of the tubular stent/graft structure of FIG. 34 taken along line 35—35.

DETAILED DESCRIPTION OF THE PREFERRED EMBODIMENTS

The present invention provides a more efficient and predictable means, as compared to the prior art, of forming a stent/graft composite device where the grafts and the stent are simultaneously formed. A planar assembly strip, having planar graft material securely fixed to a planar wire used to form a tubular structure. Because the assembly strip contains a securely fixed graft and wire, the present invention avoids some of the sealing and integrity problems inherent in the prior art as the tubular intraluminal device is created. For example, attaching planar graft material to a planar wire is more predictable, as compared to techniques in the prior art, than attaching graft material to tubular stents or even attaching tubular coverings to tubular stents. Because such a planar assembly requires positioning of surfaces and edges in only two dimensions, such a two dimensional positioning is more easily accomplished, and thus more predictable, than a three dimensional positioning. Such three dimensional positioning of both a stent/graft material is required for the techniques disclosed in the prior art where tubular stents and tubular grafts are attached to one and the other.

In some embodiments of the present invention, additional sealing of graft materials is not required after creating a tubular structure. In other embodiments, additional sealing of the graft material is required to form fluid tight conduits for use as intraluminal devices. Such additional sealing, however, is more predictable over the prior art because the assembly strip is formed into tubular shapes with well-defined seams of graft material that can be tightly sealed.

Figure 1:
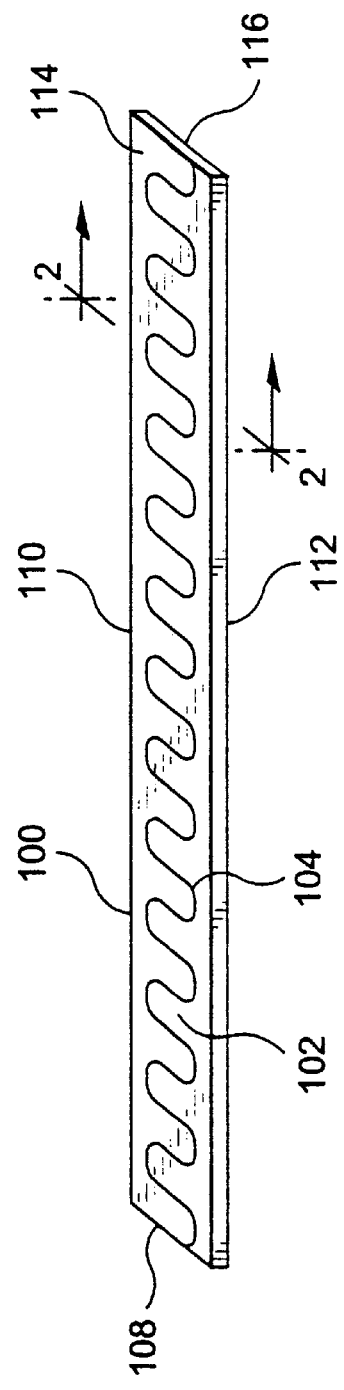
FIG. 1 is a perspective showing of one embodiment of an assembly strip of the present invention including a planar graft strip and a planar undulating wire for forming a tubular stent/graft structure for use as an intraluminal device.
Figure 2:
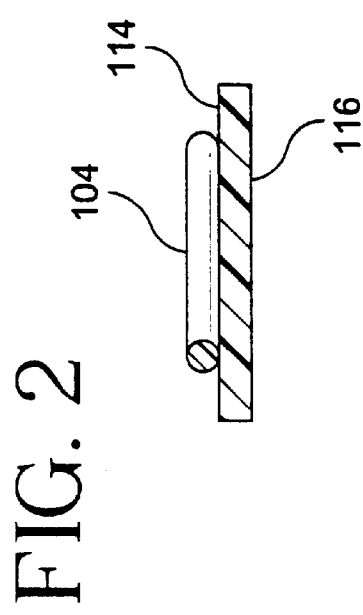
FIG. 2 is a cross-sectional view of the assembly strip of FIG. 1 taken along line 2—2.

FIGS. 1 and 2 depict a strip assembly 100 for forming a first embodiment of a tubular stent/graft apparatus of the present invention. Strip assembly 100 comprises of a planar graft strip 102 and a planar undulating wire 104. Strip assembly 100 can be formed into a tubular structure by helically winding the strip assembly 100 on a mandrel. Planar wire 104 provides, among other things, support of the graft strip 102 for use as an intraluminal device.

Assembly strips of the present invention can be produced by continuous manufacturing techniques. Long strips of the assembly strips can be cut to form the desired size of the stent/graft assembly.

As used herein, the term "wire" shall refer to stent material of a slender shape with various defined cross-sections having a cross-sectional dimension substantially less than the length of the slender shape. Such cross-sections are not limited to spherical shapes, but other shapes, such as, but not limited to, rectangular, square and oval, may suitably be used. For example, the stent material can be in the shape of a rectangular strip. Furthermore, as used herein, the term "strip" shall refer to a long narrow piece of graft material of approximately uniform breadth. For example, graft strip 102 is described as a strip because a length between a first end 106 and a second end 108 is substantially greater in dimension than the length, or breadth, between a first edge 110 and a second edge 112 of planar side 114. Also, as used herein, the term "planar" shall refer to a surface, edge or structure that can be substantially defined in two dimensions. For example, planar side 114 is described as planar because its surface is essentially flat, where it can be defined by vectors in two dimensions, not defined by a vector to any large extent a third dimension.

Planar wire 104 is disposed in substantially abutting relationship to the surface of planar side 114. Planar wire 104 may be fixed to the graft strip 102 by a variety of well-known techniques For example planar wire 104 may be fixed to the graft strip 102 by compressing the planar wire 104 thereon, by bonding the stent wire 104 thereon with adhesives or polymer solvents, followed by an application of heat, in well-known fashion. Heat may be applied to strip assembly 100 through external heating means (not shown), such as an oven. For example, a coating of fluorinated ethylene propylene (FEP) may be applied to the surface of planar side 114, and planar wire 104 may be adhesively bonded thereon with the application of heat.

Planar wire 104 is disposed onto planar side 114 in an undulated pattern. Preferably, the undulated pattern of planar wire 104 is a smooth and regular sinuous pattern, to provide, among other things, flexibility in the structure of the intraluminal device. A feature of such flexibility, imparted by an undulated planar stent wire, is that the tubular structure formed therefrom is radially adjustable. Such radial adjustability can be accomplished through use of either a self-expanding mechanism or through the use of balloon catheters, in well-known fashion. Furthermore, planar wire 104 is disposed so that it does not extend beyond edges 110 and 112 of planar side 114. Planar wire 104 is so disposed thereon to allow portions of the graft strip 102 to contact one and another as assembly strip 100 is helically wound on a mandrel to form a tubular structure.

FIGS. 3 and 4 depict the strip assembly 100 that has been helically wound. Assembly strip 100 is helically wound to form a substantially continuous tubular stent/graft structure 118. A technique for helically winding a strip assembly is described below in conjunction with FIG. 10. In a preferred embodiment, tubular stent/graft structure 118 has a generally spherical cross-section. Other cross-sectional shapes, such as, but not limited to, oval, may suitably be used.

Planar side 116 forms an exterior surface 120 of the tubular stent/graft structure 118. Planar side 114 and planar wire 104 form an interior or luminal surface 122 of the tubular stent/graft structure 118. Strip assembly 100 is helically wound on a mandrel so that successive helical windings create overlaps of graft strip 102. A portion of planar side 114 abuts a portion of planar side 116 on each successive helical winding, thereby creating an overlap. Such overlaps form a seam which can be sealed by aforementioned techniques. Upon sealing said seam, the tubular stent/graft structure 118 becomes a substantially fluid tight conduit.

Figure 5:
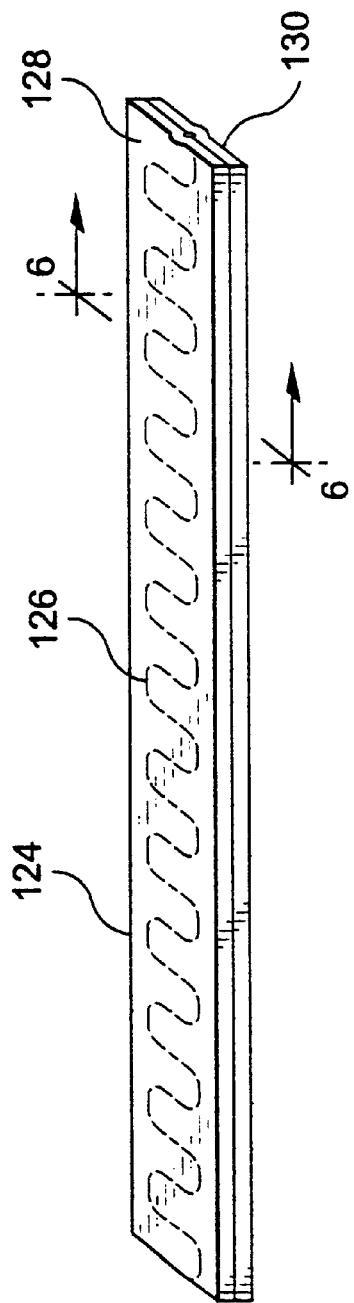
FIG. 5 is a perspective of a further embodiment of an assembly strip of the present invention containing two planar graft strips on the top and bottom surfaces of an undulating wire for forming a tubular stent/graft structure for use as an intraluminal device.
Figure 6:
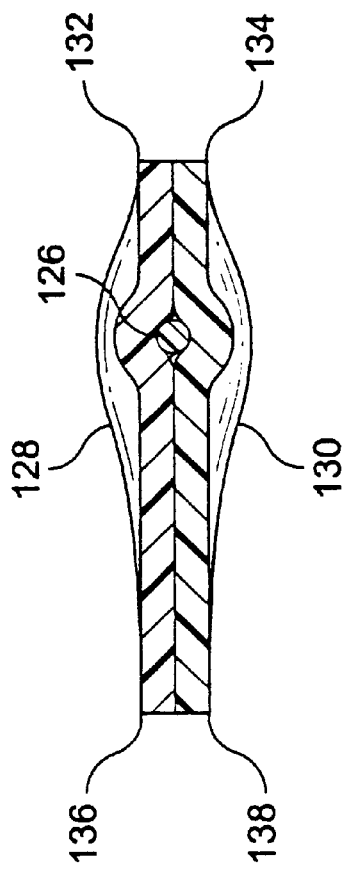
FIG. 6 is a cross-sectional view of the assembly strip of FIG. 5 taken along line 6—6.

FIGS. 5 and 6 depict a second embodiment of an assembly strip 124 for use as an intraluminal device. Assembly strip 124 comprises planar wire 126 disposed between planar graft strips 128 and 130. Planar graft strips 128 and 130 are composed of the same material as graft material 102. Planar wire 126 undulates between planar graft strips 128 and 130 along the length of said strips therebetween. Planar wire 126 is essentially planar to graft strips 128 and 130. The planar graft strips 128 and 130 may consist of multiple layers of graft material that have been laminated together to form a graft strip thereof.

Side portion 136 of planar graft strip 128 abuts side portion 138 of planar graft strip 130 along a lengthwise portion of assembly strip 124 to permit formation of a first seam on one side of assembly strip 124. Similarly, side portion 132 of planar graft strip 128 abuts side portion 134 of planar graft strip 130 to permit formation of a second seam on the other side of assembly strip 124. Such seams may be sealed by the aforementioned techniques.

Planar graft strips 128 and 130 and planar wire 126 are substantially, as depicted in FIG. 5, coplanar. Upon sealing said seams, assembly strip 124 is formed as a pre-assembly strip for use as an intraluminal device.

As depicted in FIG. 6, planar graft strip 128 and 130 are positioned so that each layer is substantially over one and the other. In an alternate embodiment planar graft strips 128 and 130 could be positioned so that one strip is offset from the other strip. Offsetting the layers is one technique for controlling the thickness of the final tubular graft and stent device because such an assembly strip can be helically wound with multiple overlaps of the strip. Furthermore, the amount of planar graft material forming an overlap can also be controlled. Such overlapping techniques are used to adjust flexibility, strength, thickness and bond integrity of the tubular graft/stent assembly.

Figure 7:
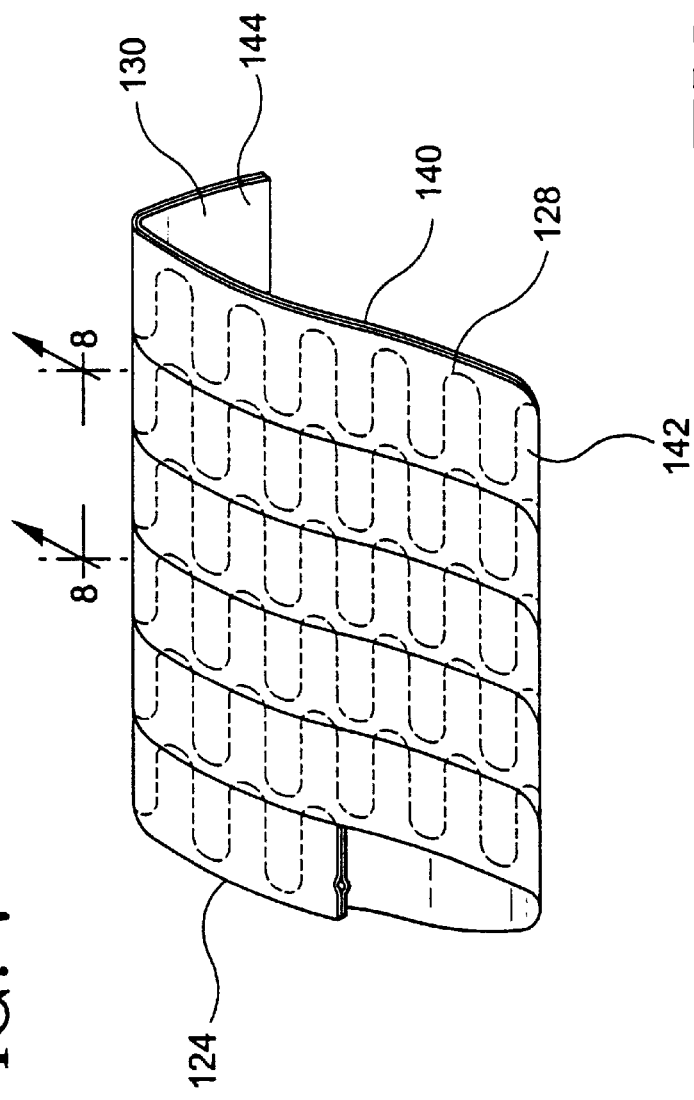
FIG. 7 is a perspective of a portion of a continuous tubular stent/graft structure formed by helically winding the assembly strip of FIG. 5.
Figure 8:
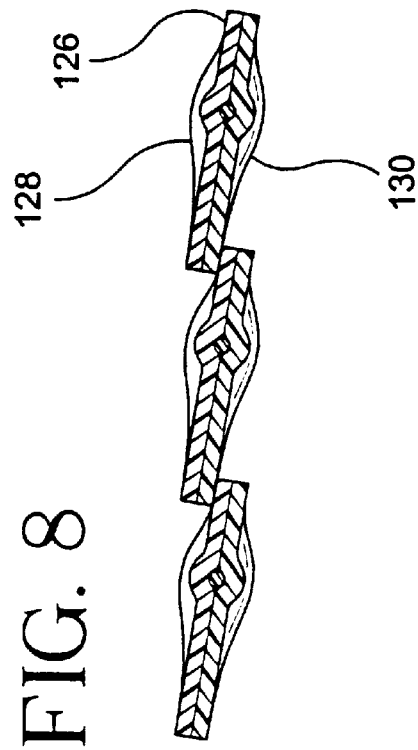
FIG. 8 is a cross-sectional view of a portion of the continuous tubular stent/graft structure of FIG. 7 taken along line 8—8.

FIGS. 7 and 8 depict strip assembly 124 that has been helically wound. Assembly strip 124 is helically wound on a mandrel to form a substantially continuous stent/graft structure 140. In a preferred embodiment, the stent/graft structure 140 is tubular with a generally spherical cross-section. Other cross-sectional shapes, such as, but not limited to, oval, may suitably be used.

Planar graft strip 128 forms an exterior surface 142 of the tubular stent/graft structure 140. Planar graft strip 130 forms an interior or luminal surface 144 of the tubular stent/graft structure 140. Strip assembly 124 is helically wound on a mandrel so that successive helical windings create overlaps with adjacent portions of strip assembly 124.

A portion of planar graft strip 128 abuts a portion of planar graft strip 130 on each successive helical winding to create the overlaps. Such overlaps form a seam which can be sealed by aforementioned techniques. Upon sealing said seam, the tubular stent/graft structure 140 becomes a substantially fluid tight conduit.

Figure 9:
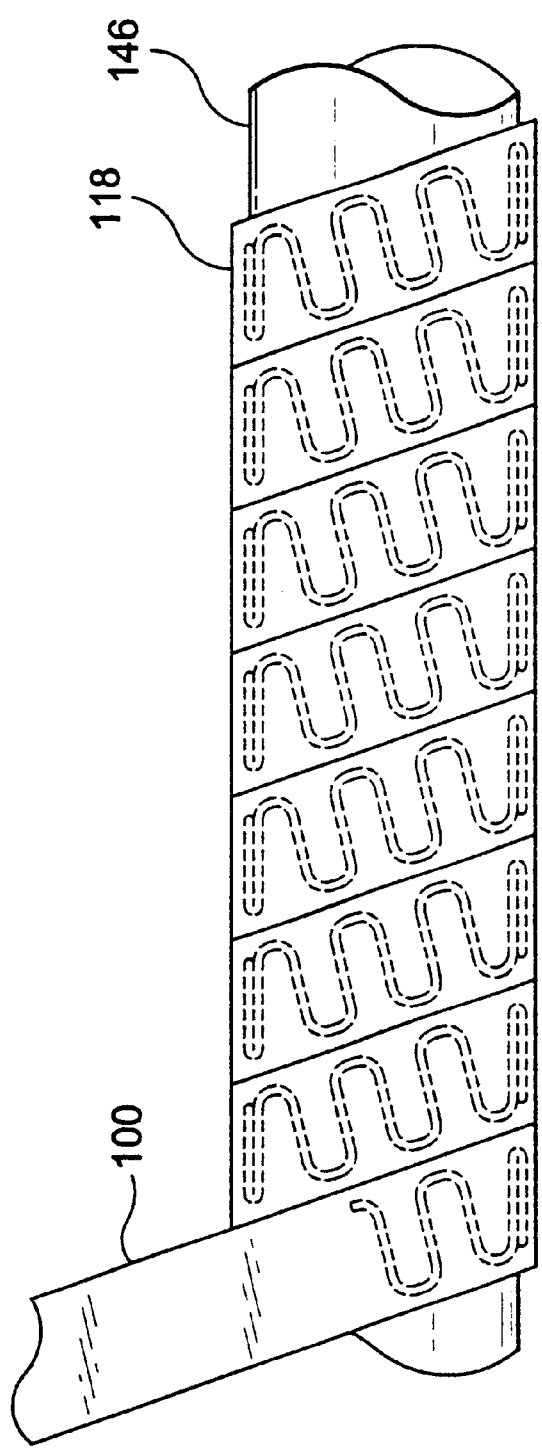
FIG. 9 illustrates a method for helically winding an assembly strip on mandrel to form a tubular stent/graft structure.

FIG. 9 depicts a method for helically winding planar assembly strips. Assembly strip 100 is helically wound about mandrel 146 to form a tubular stent/graft structure 118 with overlaps of the assembly strip 100 that form a seam. The aforementioned techniques for sealing overlaps in successive helical windings are used to form a tight fluid seam. After such seam is sealed, structure 118 is removed from mandrel 146.

FIGS. 10 and 11 depict a strip assembly 148 for forming another embodiment of a stent/graft apparatus of the present invention. Strip assembly 148 comprises planar graft strip 150 and planar wire 152. Planar wire 152, as depicted in FIG. 11, is disposed in substantially abutting relation to planar side 154 of the graft strip 150. Furthermore, planar wire 152 is disposed in a substantially straight lengthwise pattern along the length of the graft strip 150. Planar wire 152 is fixed onto the planar side 154 by aforementioned techniques. The straight-lengthwise pattern of planar wire 152 provides for, among other things, flexibility and longitudinal adjustability of the tubular intraluminal device formed therefrom by helically winding techniques.

Figure 13:
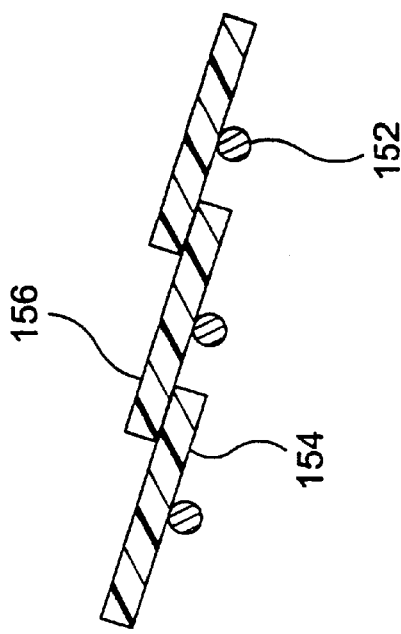
FIG. 13 is a cross-sectional view of a portion of the continuous tubular stent/graft structure of FIG. 12 taken along line 13—13.
Figure 12:
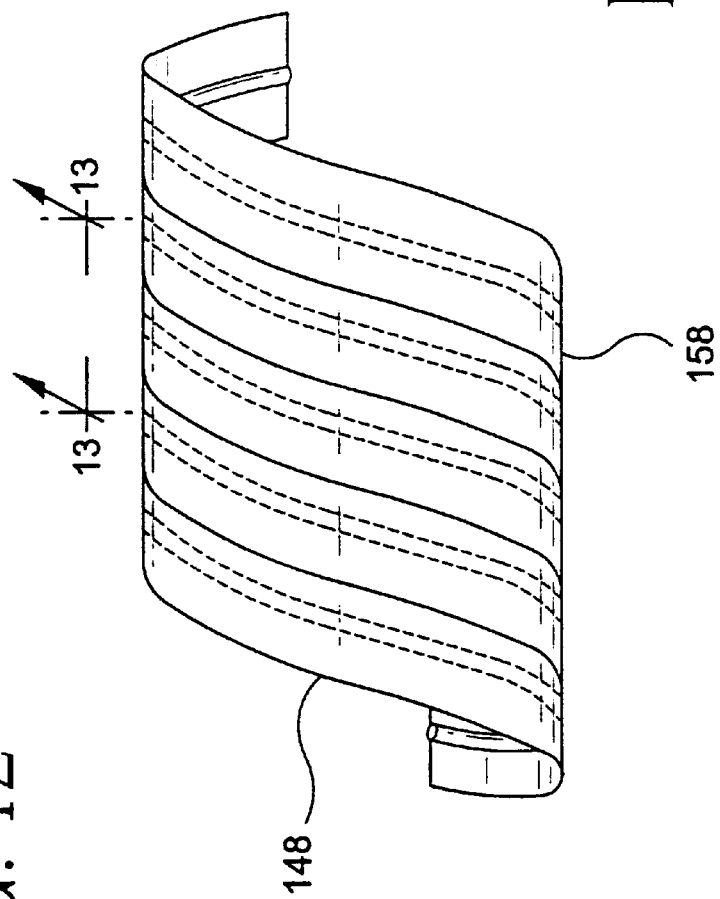
FIG. 12 is a perspective of a portion of a continuous tubular stent/graft structure formed by helically winding the assembly strip of FIG. 10.

As depicted in FIGS. 12 and 13, assembly strip 148 may be helically wound on a mandrel to form a substantially tubular and continuous stent/graft structure 158 with a generally spherical cross-section. As depicted in FIG. 13, which is a view of cross-section 13—13 of the tubular stent/graft structure 158, a portion of planar side 154 of assembly strip 148 abuts a portion of planar side 156 of assembly strip 148 on each successive wind to create overlaps in strip assembly 148. Such overlaps form a seam. Upon sealing said seam by aforementioned techniques, the tubular stent/graft structure 158 becomes a substantially fluid tight conduit.

Figure 14:
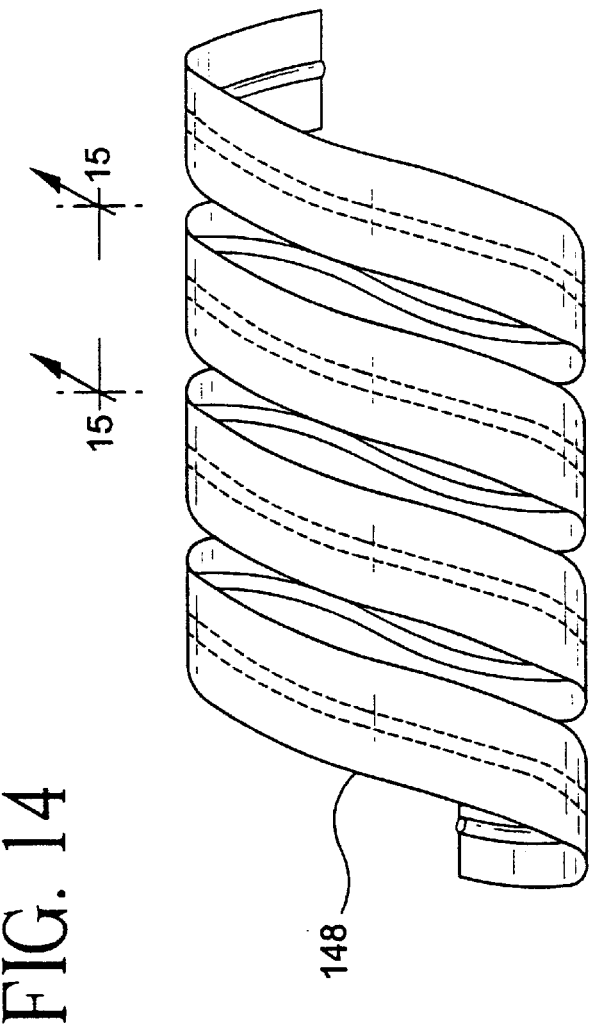
FIG. 14 is a perspective of a portion of a tubular stent/graft structure formed by helically winding the assembly strip of FIG. 10 without overlapping adjacent graft strip portions.
Figure 15:
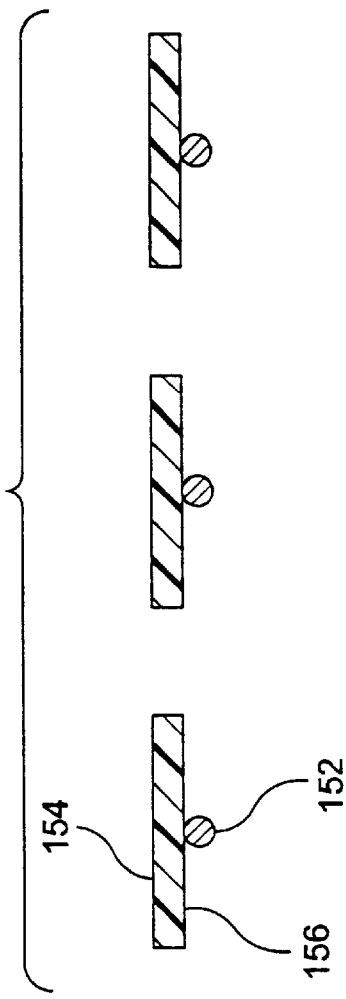
FIG. 15 is a cross-sectional view of a portion of the tubular stent/graft structure of FIG. 14 taken along line 15—15.

As depicted in FIGS. 14 and 15, the assembly strip 148 may be helically wound so that successive windings do not overlap, thereby forming a tubular stent/graft structure 160 without overlapping adjacent graft strip portions. Such non-overlapping windings allow the tubular stent/graft structure 160, among other things, to be longitudinally adjustable through use of either a self-expanding mechanism or through a pulling or pushing action by a physician, in well-known fashion.

Other embodiments of longitudinally adjustable intraluminal devices are shown in FIGS. 16 through 21.

Figure 16:
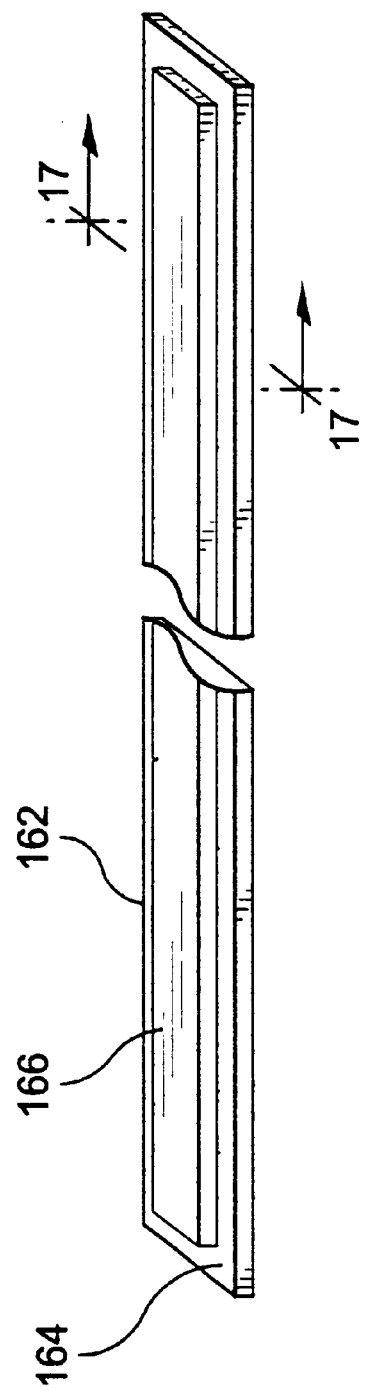
FIG. 16 is perspective showing of a further embodiment of an assembly strip of the present invention having a planar graft strip and a planar ribbon stent strip for forming a tubular stent/graft structure.
Figure 17:
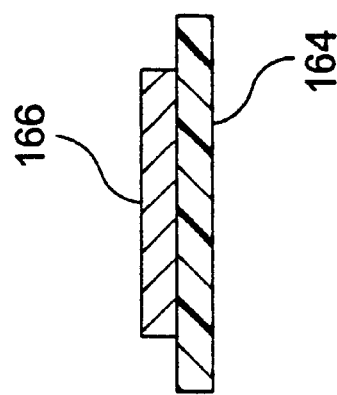
FIG. 17 is a cross-sectional view of the assembly strip of FIG. 16 taken along line 17—17.
Figure 18:
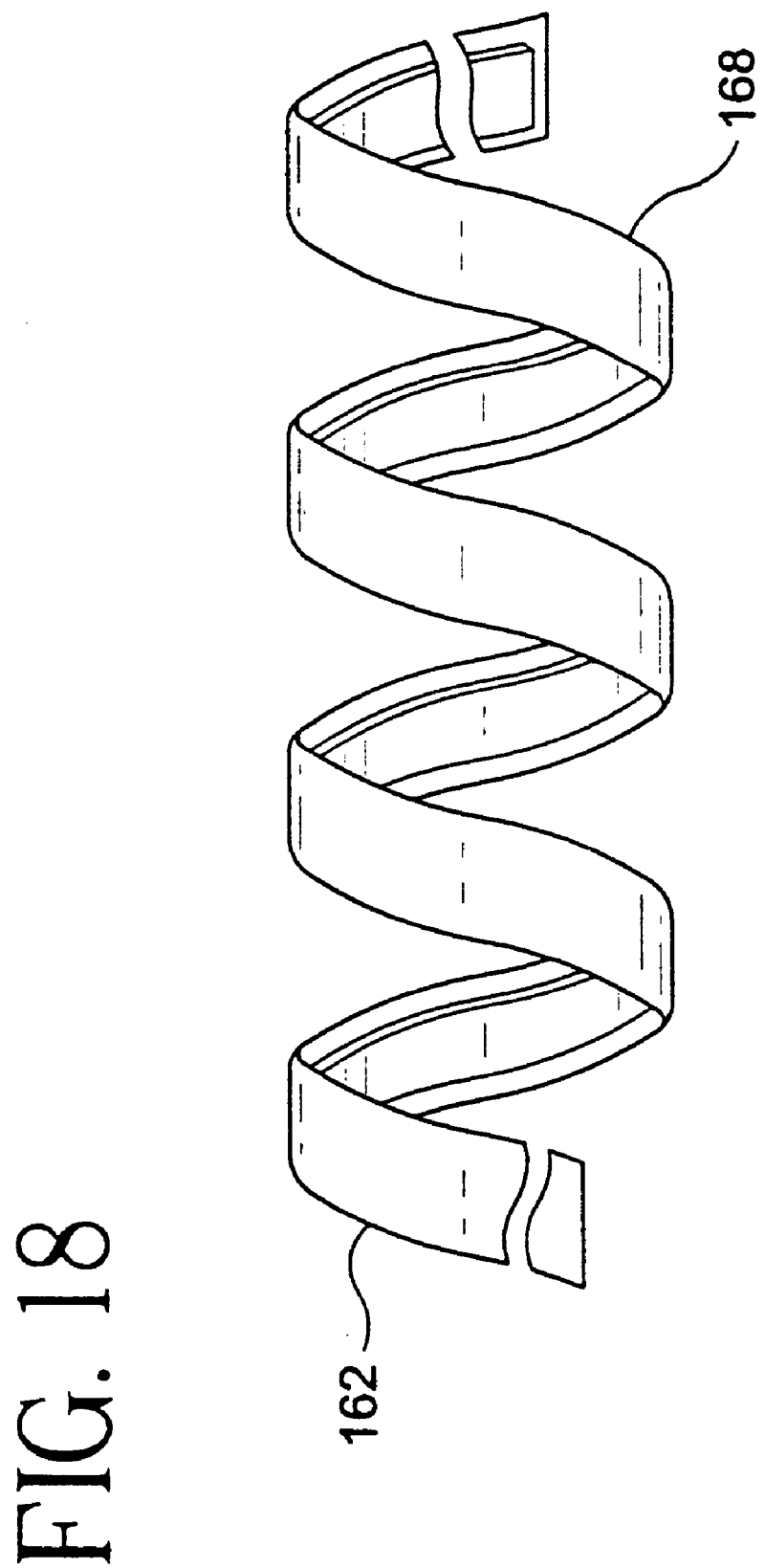
FIG. 18 is an illustration of a portion of a tubular stent/graft structure formed by helically winding the assembly strip of FIG. 16 without overlapping adjacent graft strip portions.

As depicted in FIGS. 16 and 17, assembly strip 162 comprises a planar graft strip 164 and a planar ribbon stent strip 166. The planar ribbon stent strip 166 is disposed in substantially abutting relation, to the planar graft strip 164. Planar ribbon stent strip 166 may be secured to a surface of the planar graft strip 164 by aforementioned techniques. Upon helically winding assembly strip 162 on a mandrel, a tubular stent/graft structure 168, as depicted in FIG. 18, is formed without overlapping adjacent graft strip portions.

Figure 19:
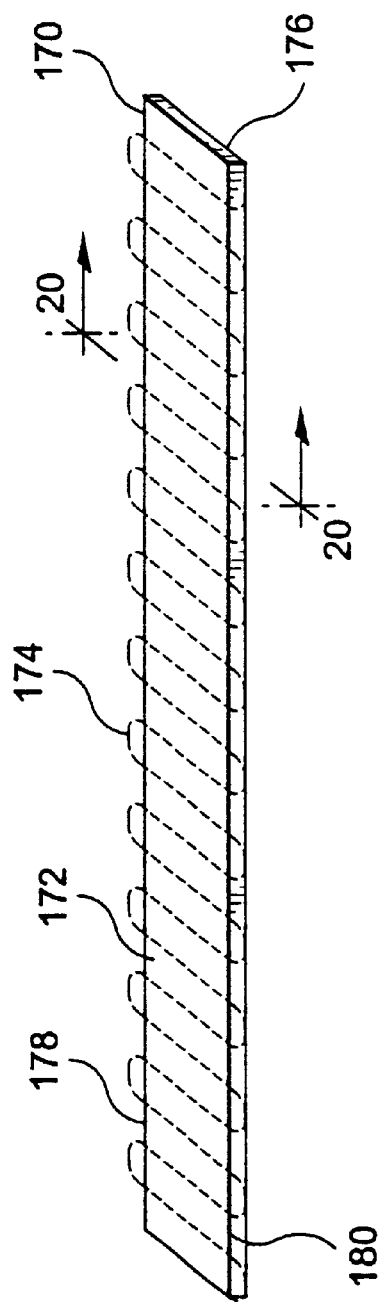
FIG. 19 is perspective showing of yet a further embodiment of an assembly strip of the present invention for forming a tubular stent/graft structure having non-overlapping adjacent graft strip portions.
Figure 20:
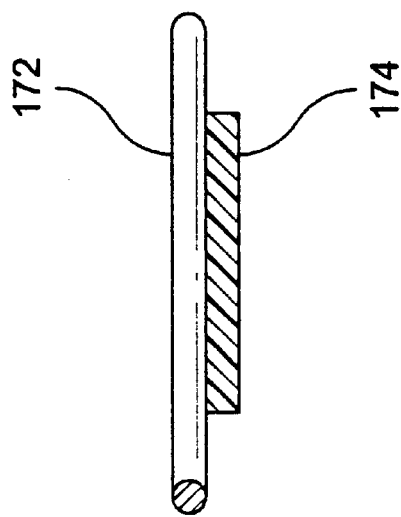
FIG. 20 is a cross-sectional view of the assembly strip of FIG. 19 taken along line 20—20.

FIGS. 19 and 20 depict planar wire 174 which undulates along planar side 176 of planar graft strip 172.

Figure 21:
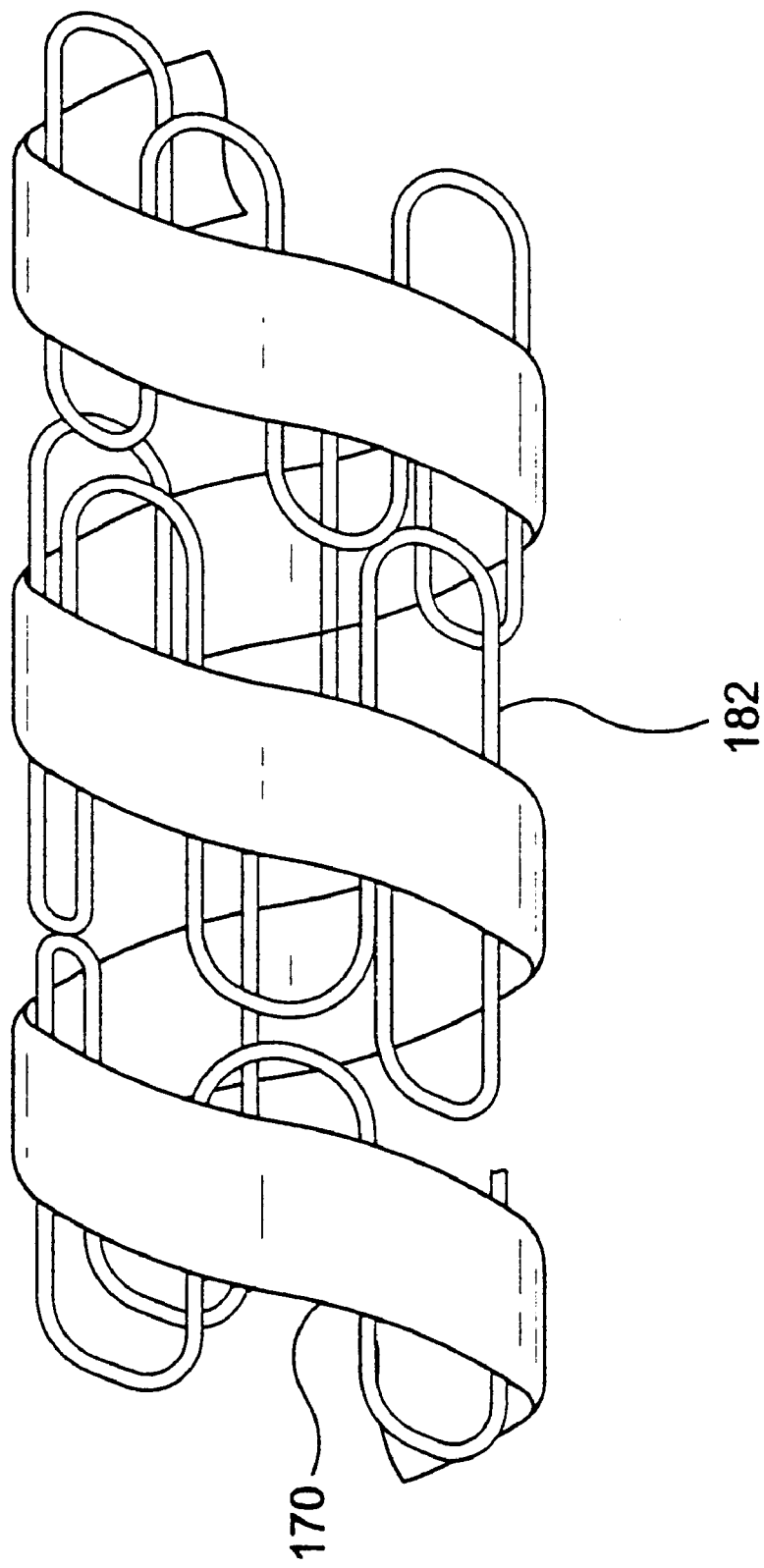
FIG. 21 is an illustration of a portion of a tubular stent/graft structure formed by helically winding the assembly strip of FIG. 19 without overlapping adjacent graft strip portions.

Planar wire 174 extends or protrudes beyond edges 178 and 180 of the planar strip 172. Upon helically winding assembly strip 170, a tubular stent/graft structure 182 without overlapping adjacent graft strip portions, as depicted in FIG. 21, is formed. Tubular stent/graft structures 168 and 182 are, among other things, longitudinally adjustable because no seals are formed at adjacent graft strip portions of the tubular structures.

Figure 22:
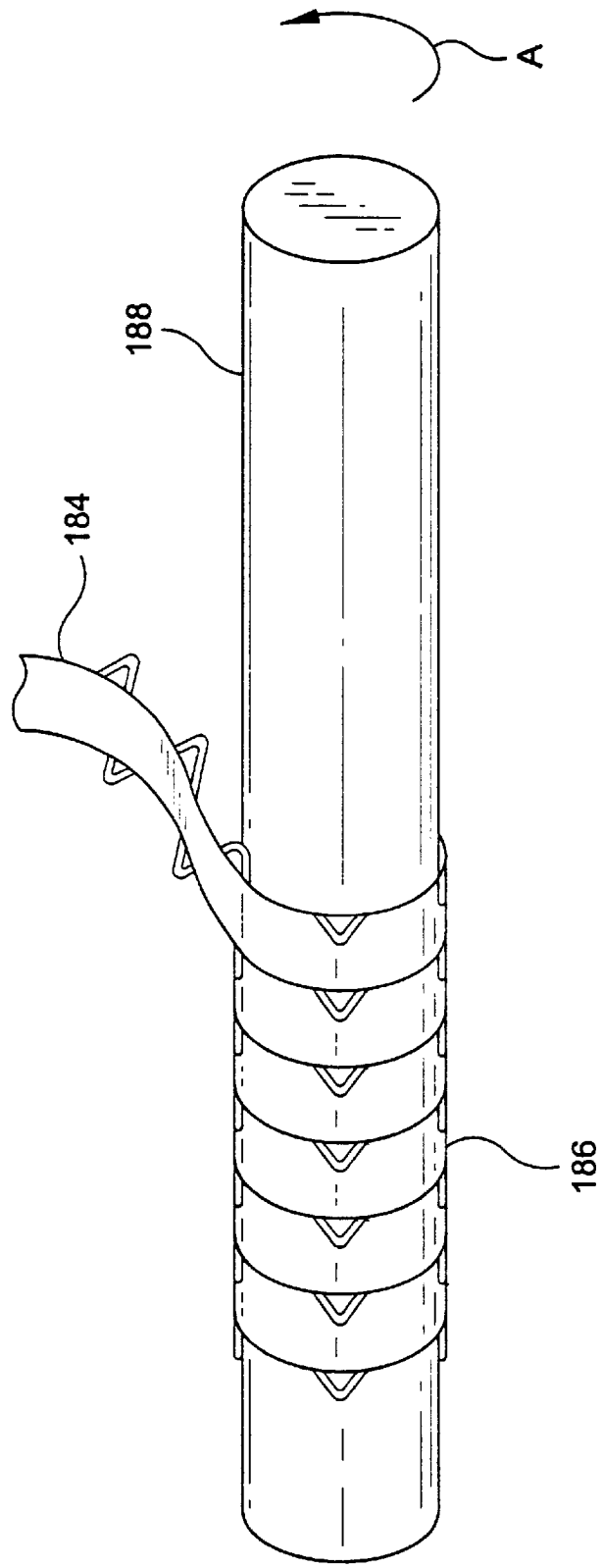
FIG. 22 illustrates a method for helically winding about a mandrel an assembly strip having a stent wire protruding beyond a graft strip for forming a tubular stent/graft structure.

As depicted in FIG. 22, assembly strip 184 may be helically would on a mandrel 188 to form a tubular stent/graft structure 186, where adjacent portions of assembly strip 184, are proximally located to one end and the other, or even overlap one and the other. The tubular stent/graft structure 186 may be longitudinally expanded to form tubular stent/graft structure without adjacent overlapping graft strip portions, as depicted in FIG. 21. Furthermore, the tubular stent/graft structure 182 is radially adjustable because of the undulated planar stent wire 174.

FIGS. 23 through 34 depict additional embodiments of the present invention for forming fluid tight intraluminal devices.

Figure 24:
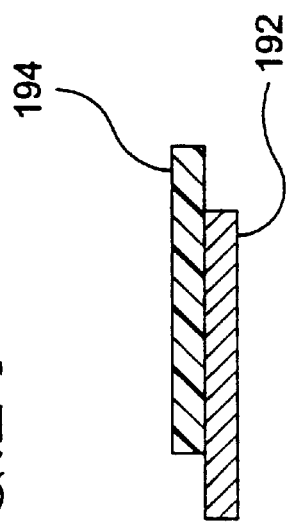
FIG. 24 is a cross-sectional view of the assembly strip of FIG. 23 taken along 24—24.
Figure 23:
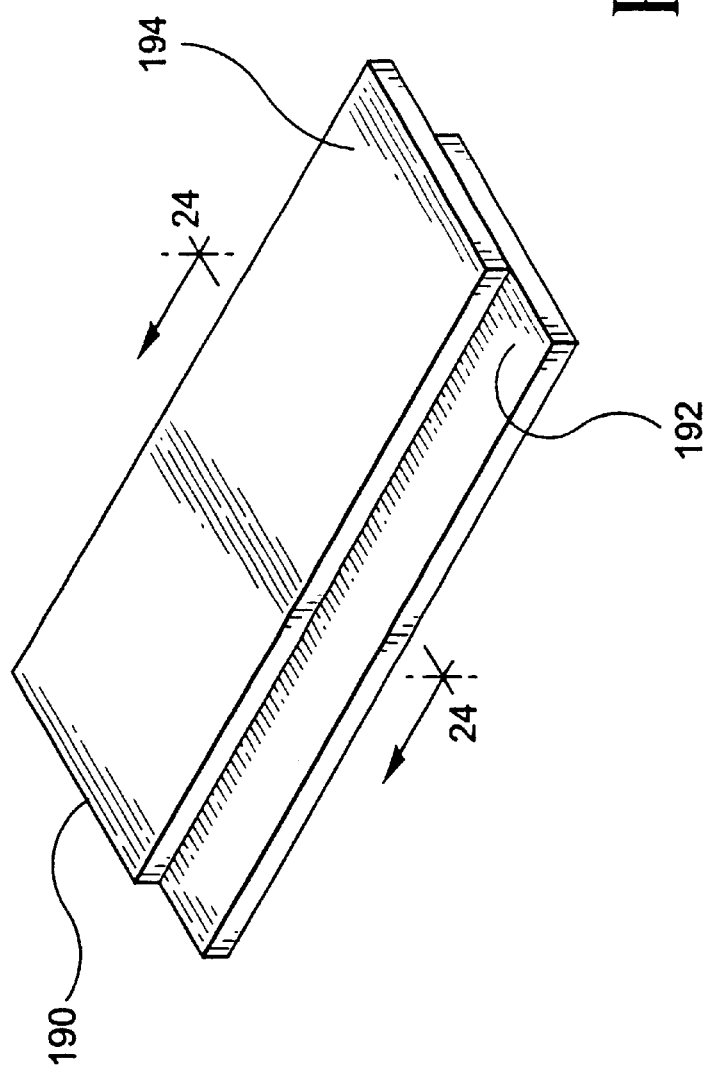
FIG. 23 is a perspective showing of an additional embodiment of an assembly strip of the present invention having a planar graft strip and an overlapping planar ribbon stent strip for forming a continuous tubular stent/graft structure.
Figure 25:
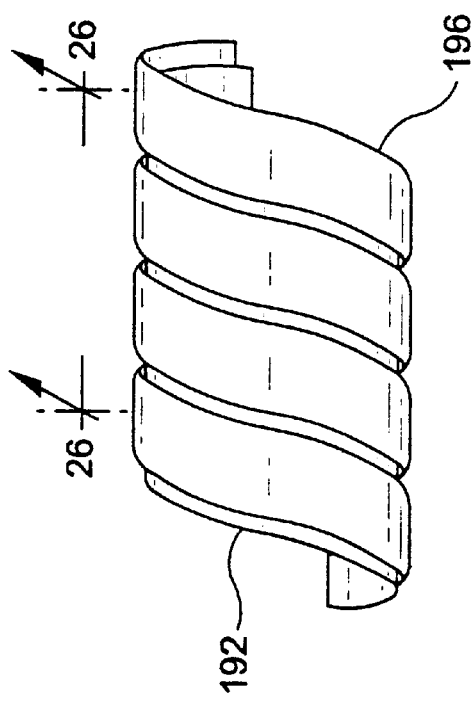
FIG. 25 is an illustration of a portion of a continuous tubular stent/graft structure formed by helically winding the assembly strip of FIG. 23.
Figure 26:
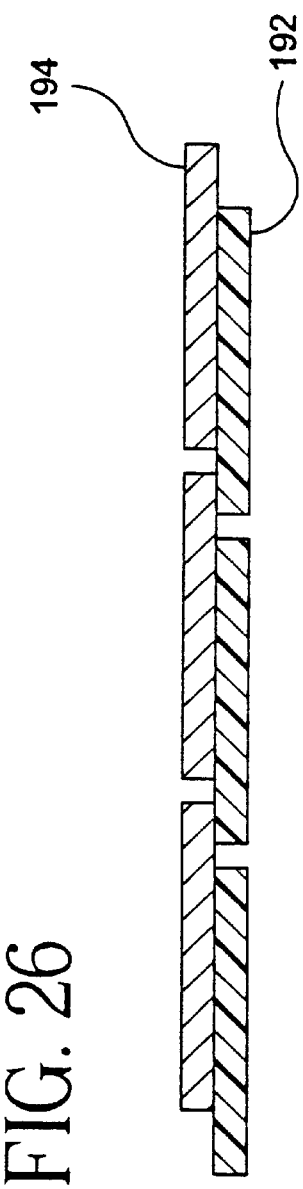
FIG. 26 is a cross-sectional view of a portion of the continuous tubular stent/graft structure of FIG. 25 taken along line 26—26.

As depicted in FIGS. 23 and 24, assembly strip 190 comprises planar graft strips 192 and 194. The planar graft strip 192 abuts the overlapping planar ribbon stent strip 194 and may be disposed thereon by aforementioned techniques. As depicted in FIG. 25, a continuous tubular stent/graft structure 196 may be formed by helically winding assembly strip 190. Successive helical windings on a mandrel create overlaps of adjacent portions of the graft strip 192 and the planar ribbon stent strip 194, which may be sealed by aforementioned techniques to form fluid tight conduits.

As depicted in FIGS. 27–30, an assembly strip 198 may be formed from planar graft strip 200 and planar ribbon stent strip 202. The planar ribbon stent strip 202 contains cuffs 204 and 206 that abut portions of the planar graft strip 200. Upon fixing the cuffs 204 and 206 to the planar graft strip 200 by aforementioned techniques, the assembly strip 198 is formed. A continuous structure 208, as depicted in FIG. 29, may be formed by successively winding assembly strip 198 on a mandrel in a manner where side portions of the planar graft strip 200 and the planar ribbon stent strip 202 abut with each successive winding, thereby forming a seam. Such a seam may be sealed by the aforementioned techniques to form a fluid tight conduit.

Figure 33:
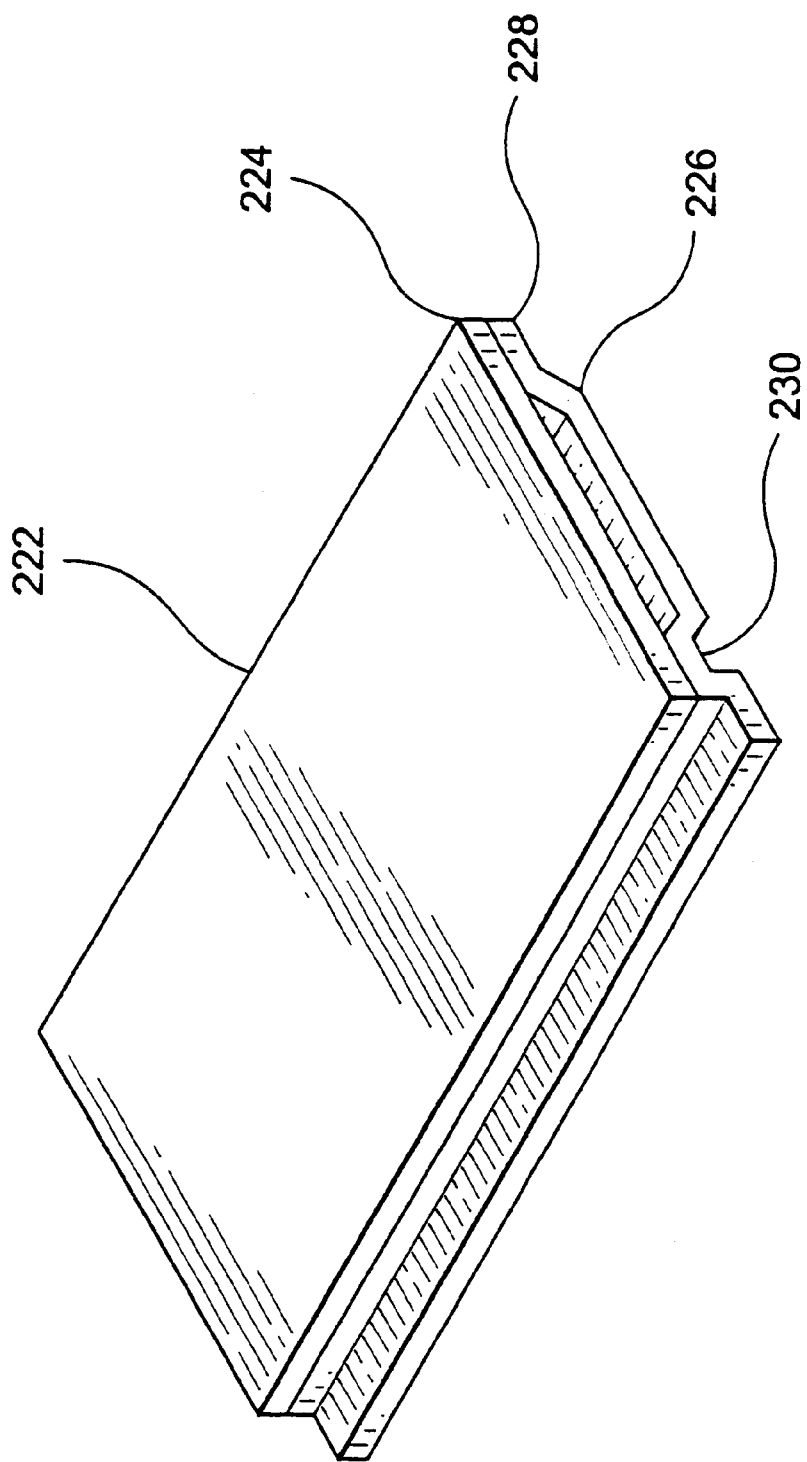
FIG. 33 is a perspective showing, partially in section of an assembly strip having a planar graft strip and a planar ribbon stent strip with two longitudinal folds for forming a tubular stent/graft structure.

Fluid tight conduits for use as intraluminal devices may be formed where the interior or luminal surface is substantially continuous, such as structure 210 as depicted in FIG. 32, or where the exterior surface is substantially continuous, such as structure 220 as depicted in FIG. 34. Such devices with substantially continuous luminal and exterior surfaces may be formed by sealing overlaps formed by helically winding assembly strips 212 and 222, respectively. The continuity of either the luminal or external surface is controlled by altering the planar ribbon stent strips, e.g., stent strips 216 and 226, as depicted in FIGS. 31 and 33. For example, planar ribbon stent strip 216 has a longitudinal fold 218 along one of its sides. The fold 218 is configured so that a portion of the fold 218 abuts a portion of planar graft strip 214 on each successive helical winding to allow the remaining portions of planar ribbon stent strip 216 to form tubular structure with a substantially continuous luminal surface.

An intraluminal device with a substantially smooth and continuous exterior surface may be formed from assembly strip 222. As depicted in FIG. 33, the assembly strip 222 consists of a planar graft strip 224 and a planar ribbon stent strip 226. Planar stent strip 226 contains a longitudinal fold 228 along one side of its lengthwise portion, a longitudinal fold 230 along the other side of its lengthwise portion. Upon helically wind the assembly strip 222, the continuous tubular stent/graft structure 220 is formed. As depicted in FIG. 35, which is a cross-sectional view of a portion of structure 220, longitudinal folds 228 and 230 overlap one and the other on each adjacent helical winding. Side portions of planar graft strip 224 also abut one and the other on each adjacent helical winding to form a substantially continuous and smooth exterior surface.

The non-woven polymeric graft material may be formed by any conventional method provided the method allows for a porous surface structure to remain or be created. For example, extrusion processes such as ram extrusion; polymeric casting techniques such as solvent casting and film casting; molding techniques such as blow molding, injection molding and rotational molding; and other thermoforming techniques useful with polymeric materials may be employed and chosen to best serve the type of material used and specific characteristics of the membrane desired. Graft strips may also be formed by laminating multiple layers of graft material.

The preferred membrane material of the present invention is ePTFE, although other thermoformable polymeric materials such as porous polyurethane and the like may be employed. The orientation of the fibers forming such polymeric materials can be varied to have the orientation of the fibers in an axial direction of the tubular structure, a longitudinal orientation or some combination thereof.

The porous membranes of the present invention need not be structurally sufficient per se to withstand the pressures of blood flow and may be used merely as thin covers or liners for the stents and other devices in applications where dislodging of plaque debris and/or regrowth of the occlusion through the stent wall is of concern. Thus, in one embodiment, the membrane may have the structural integrity of a typical endoprosthesis or vascular graft, and in another embodiment the membrane may be of a thinner wall thickness than a typical vascular graft, but sufficient in thickness to serve as a prophylactic liner or cover against the aforementioned debris.

The stent may be made from a variety of materials including stainless steel, titanium, platinum, gold and other bio-compatible metals. Thermoplastic materials which are inert in the body may also be employed. Shaped memory alloys having superelastic properties generally made from specific ratios of nickel and titanium, commonly known as nitinol, are among the preferred stent materials.

Various stent types and stent constructions may be employed in the invention. Among the various stents useful include, without limitation, self-expanding stents and balloon expandable extents. The stents may be capable of radially contracting, as well and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents.

The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like.

The assembly strips of the present invention are not limited to the use of one stent wire positioned onto an assembly strip. A plurality of stent wires may be fixed onto assembly strips to achieve desired stent patterns.

Various changes in modifications may be made to the invention, and it is intended to include all such changes and modifications as come within the scope of the invention and as set forth in the following claims.

What is claimed is:

1. A stent/graft composite device formed from a flat preformed planar strip and wire assembly comprising:
an elongate preformed non-textile planar strip of polymeric graft material having first and second opposed surfaces and an elongate stent wire attached onto one of said opposed flat surfaces of said strip to form said flat strip assembly, said strip assembly being helically wound into a continuous tubular structure.

2. The device of claim 1 wherein successive helical windings creates an overlap defining a seam between an exterior surface of a first helical wind and a luminal surface of a subsequent helical wind.

3. The device of claim 1 further comprising a second elongate preformed planar strip of graft material, wherein said wire stent is positioned between the two planar graft strips.

4. The device of claim 3 wherein said planar graft strips are laminated together to form said strip assembly.

5. The device of claim 4 wherein said planar graft strips further include multiple layers of graft material on each side of said stent wire.

6. The device of claim 1 wherein said polymeric graft material is selected from the group consisting of fluoropolymers, polyurethanes, silicones and mixtures thereof.

7. The device of claim 1 wherein said polymeric graft material comprises ePTFE.

8. The device of claim 1 wherein said tubular structure has a generally circular cross-section.

9. The device of claim 1 wherein said stent wire has a series of bends forming undulations along its length.

10. The device of claim 9 wherein said undulations have flexibility capable of providing a radially adjustable tubular stent/graft apparatus.

11. The device of claim 1 wherein said stent wire is comprised of nitinol.

12. A covered stent assembly formed from a flat planar strip and wire assembly comprising a length of a planar preformed non-textile cover strip of polymeric graft material having first and second opposed flat surfaces and a length of wire attached onto one of said opposed flat surfaces along the length of said strip to form said flat planar strip and wire assembly, said strip and wire assembly being helically wound forming windings and further forming a continuous tubular structure.

13. The covered stent assembly of claim 12 wherein said strip and wire assembly is helically wound having at least two consecutive windings overlap.

14. The covered stent assembly of claim 13 wherein adjacent windings form a continuous tubular and substantially fluid tight conduit.

15. The covered stent assembly of claim 12 wherein consecutive windings do not overlap.

* * * * *